US00PP08943P

United States Patent [19]

Olesen et al.

[11] Patent Number: Plant 8,943

[45] Date of Patent: Oct. 18, 1994

[54] MINIATURE ROSE PLANT NAMED 'POULANN'

[75] Inventors: Mogens N. Olesen; Pernille Olesen, both of Fredensborg, Denmark

[73] Assignee: Bear Creek Gardens, Inc., Medford, Oreg.

[21] Appl. No.: 96,927

[22] Filed: Jul. 23, 1993

[51] Int. Cl.[5] ..... A01H 5/00

[52] U.S. Cl. ..... Plt./9

[58] Field of Search ..... Plt. 7.1, 9, 10

*Primary Examiner*—Howard J. Locker

*Attorney, Agent, or Firm*—Klarquist Sparkman Campbell Leigh & Whinston

[57] ABSTRACT

A rose plant of the miniature class, a sport of the variety POULvic, having a different flower color from its parent.

1 Drawing Sheet

The present invention relates to a new and distinct variety of rose plant of the miniature class which was discovered by us as a mutation of the variety POULvic, U.S. Plant Pat. No. 8,012.

This variety is unique and distinct from its parent variety, POULvic, principally in its flower color. Instead of having petals that are of Red Group 45C color, the petals are Purple-Red Group 58C on their upper sides and Purple-Red Group 55B on their reverse sides.

Asexual reproduction of this new variety by softwood cuttings, as performed at Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Classification:

*Botanical.*—*Rosa hybrida.*

*Commercial.*—Miniature.

FLOWER

Observations made from specimens grown in a greenhouse environment at Fredensborg, Denmark, in 1989.

Blooming habit: Continuous.

Bud:

*Size.*—1.6 cm long when the petals start to unfurl.

*Form.*—Pointed ovoid.

*Color.*—When sepals first divide, bud color is Red-Purple Group 589C. When half blown, the upper sides of the petals are Red-Purple Group 58C; and the lower sides of the petals are Red Group 55C.

*Sepals.*—Color: Green Group 138B. Surface texture: Covered in fine hairs. There are three lightly appendaged sepals. There are two unappendaged sepals with hairy edges.

*Receptacles.*—Color: Green Group 138A. Shape: Apple. Size: Small. Surface: Smooth.

*Peduncle.*—Length: Very long, for a pot rose. Surface: Smooth, prickly. Color: Medium green. Strength: Stiff, erect.

Bloom:

*Size.*—Small. Average open size is 3.5 cm in diameter.

*Borne.*—Several together, in flat clusters of 4 to 10 or more flowers.

*Stems.*—Medium (average length 15 cm), strong.

*Form.*—When first open: High centered. Permanence: Flattens, all petals curl.

*Petalage.*—Number of petals under normal conditions: 30 to 40.

*Color.*—The upper side of the petals is Red-Purple Group 58C. The reverse side of the petals is Red-Purple Group 55B. The base of petals is Yellow Group 4D. The major color on the upper side is Red-Purple Group 58C.

*Variegations.*—None.

*Discoloration.*—There is no change in general tonality at the end of the first day. At the end of the third day, general tonality fades to Red Group 55B.

*Fragrance.*—Slight.

Petals:

*Texture.*—Leathery.

*Shape.*—Pointed.

*Form.*—Moderately quilled.

*Arrangement.*—Regularly arranged, with few petaloids in the center.

*Persistence.*—Drop off cleanly.

*Lastingness.*—On the plant: Very long (10 to 14 days). As a cut flower: Very long (9 to 12 days).

Reproductive parts:

*Anthers.*—Size: Medium. Quantity: Many. Color: White, yellow. Arrangement: Regular around styles; mixed with petaloids.

*Filaments.*—Color: White, yellow.

*Pollen.*—Color: Gold yellow.

*Styles.*—Color: Greenish white.

*Stigmas.*—Color: Greenish white.

Form: Bush.

Growth: Dwarf.

Foliage:

*Number of leaflets on normal mid-stem leaves.*—5.

*Size.*—Small.

*Quantity.*—Normal.

*Color.*—New foliage: RHS Green Group 138B with a reddish tinge, especially on leaftlet edges. Old foliage: Top: RHS Green Group 139A; reverse: RHS Green Group 138C.

Leaflets:

Shape.—Oval pointed.

*Texture.*—Upper side: Glossy.

*Edge.*—Serrated.

*Serrations.*—Single, small.

*Petiole rachis.*—Color: Reddish.

*Petiole underside.*—With prickles.

*Stipules.*—Medium, bearded.

*Disease resistance.*—Resistance to mildew under normal greenhouse conditions in Denmark and in Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Few.

*Form.*—Medium, straight.

*Color when young.*—Brown at the base shading to green and finally red at the tip.

Small prickles:

*Quantity.*—On main stalks: Many. On laterals: Few.

*Color.*—Brown.

We claim:

1. A new and distinct variety of rose plant of the miniature class, substantially as herein shown and described, a sport of the variety POULvic, characterized particularly as to novelty by its flower color difference from its parent.

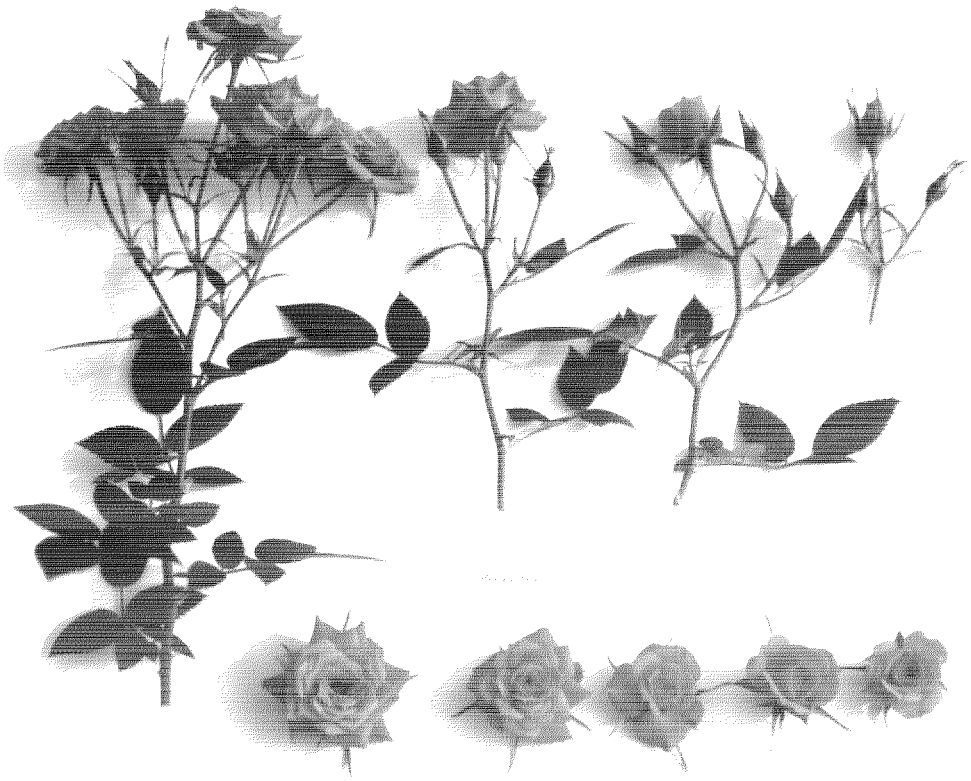

* * * * *